United States Patent [19]

Naumann

[11] 4,236,026
[45] Nov. 25, 1980

[54] SEPARATION OF STEREOISOMERIC VINYLCYCLOPROPANECARBOXYLIC ACIDS

[75] Inventor: Klaus Naumann, Cologne, Fed. Rep. of Germany

[73] Assignee: Bayer Aktiengesellschaft, Leverkusen, Fed. Rep. of Germany

[21] Appl. No.: 970,099

[22] Filed: Dec. 15, 1978

[30] Foreign Application Priority Data

Jan. 10, 1978 [DE] Fed. Rep. of Germany ....... 2800922

[51] Int. Cl.$^3$ .............................................. C07B 19/00
[52] U.S. Cl. ..................................... 562/401; 562/506
[58] Field of Search ................................ 562/401, 506

[56] References Cited

U.S. PATENT DOCUMENTS

| | | | |
|---|---|---|---|
| 3,636,093 | 1/1972 | Hoinowski et al. | 562/401 |
| 3,646,118 | 2/1972 | Goffinett et al. | 562/401 |
| 3,739,019 | 6/1973 | Ueda et al. | 562/401 |
| 3,842,125 | 10/1974 | Horiuchi et al. | 562/401 |
| 4,002,666 | 1/1977 | Shirai et al. | 562/401 X |
| 4,118,417 | 10/1978 | Epstein | 562/401 |

FOREIGN PATENT DOCUMENTS 2432951 1/1975 Fed. Rep. of Germany .
2439177 2/1975 Fed. Rep. of Germany .
2615159 10/1976 Fed. Rep. of Germany .
1446304 8/1976 United Kingdom .

OTHER PUBLICATIONS

J. Org. Chem., 17, pp. 381–389, (1952).
Coll. Czech. Chem. Commun., 24, pp. 2230–2235 & 3236, (1959).
J. Chem. Soc., 1945, pp. 283–286.
Pestic. Sci., 1971, vol. 2, Nov.-Dec., pp. 243–248.
J. Agr. Food Chem., 21, pp. 767–769, (1973).
Pestic. Sci., 1974, 5, pp. 791–799.

Primary Examiner—Natalie Trousof
Assistant Examiner—Vera C. Clarke
Attorney, Agent, or Firm—Sprung, Felfe, Horn, Lynch & Kramer

[57] ABSTRACT

A process for the separation of the cis- and trans-stereoisomers of a substituted vinylcyclopropanecarboxylic acid of the formula

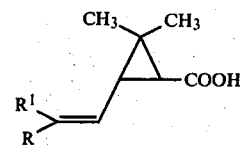

in which
R is alkyl with 1 to 4 carbon atoms, halogen, phenyl or phenyl substituted by at least one of alkyl and halogen, and
$R^1$ is hydrogen, alkyl with 1 to 4 carbon atoms or halogen, or
R and $R^1$, together with the adjacent C atom, form a carbocyclic ring, comprising reacting the free vinylcyclopropanecarboxylic acid in a weakly alkaline aqueous solution with an amount of an amine salt corresponding to the proportion of the cis-isomer present thereby to form a salt precipitate enriched in one of the stereoisomers, separating the precipitant from the supernatant, separately reacting the precipitate and supernatant with a strong acid to liberate the isomeric vinylcyclopropanecarboxylic acid, and recrystallizing at least one of the stereoisomers.

10 Claims, No Drawings

SEPARATION OF STEREOISOMERIC VINYLCYCLOPROPANECARBOXYLIC ACIDS

The present invention relates to an unobvious process for the separation of known substituted vinylcyclopropanecarboxylic acids into their stereoisomers.

It has already been disclosed that mixtures of stereoisomeric cis-substituted and trans-substituted cyclopropanecarboxylic acids can be separated by fractional crystallization. (Coll. Czech. Chem. Commun. 24, 2230 (1959); Pestic. Sci. 1971, 245; Pestic. Sci. 1974, 791; and DOS (German Published Specification) 2,439,177). However, this process is troublesome and wasteful. This process is not suitable for obtaining relatively large amounts of pure trans-isomers or cis-isomers.

It is also already known that certain optically active acids can be resolved into their salts with amines on the basis of their different solubility. However, it was not known that cis/trans-isomers of cyclopropanecarboxylic acids can be separated in this manner.

It has now been found that the stereoisomers of substituted vinylcyclopropanecarboxylic acids of the general formula

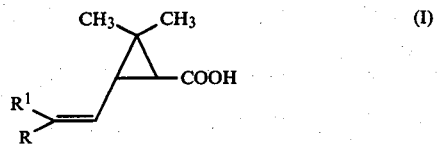

in which
R represents alkyl with 1 to 4 C atoms, halogen or phenyl which is optionally substituted by alkyl (especially of 1 to 4 C atoms) and/or by halogen and
$R^1$ represents hydrogen, alkyl with 1 to 4 C atoms or halogen, or
R and $R^1$, together with the adjacent C atom, form a carbocyclic ring, and wherein the substituents in the ring in the cis-position or trans-position and the molecules can also exist in the optically active form, can be separated in a simple manner by a process in which the five vinylcyclopropanecarboxylic acids are reacted with an amount of an amine salt corresponding to the proportion of cis-isomer in a weakly alkaline, (i.e. the range between pH 7 and 9) aqueous solution, the corresponding cis/trans-isomeric salts are separated from one another on the basis of their different solubility and the cis-isomeric and trans-isomeric vinylcyclopropane-carboxylic acids are liberated with the aid of strong acids and recrystallized.

Preferably, R and $R^1$ in the formula (I) each represent chlorine, bromine or methyl.

It is surprising that it is possible to separate the cis-isomeric acid from the trans-isomeric acid by the process according to the invention, since it could not be foreseen that the difference in the solubility of the cis/trans-isomeric salts was so great.

Furthermore, it is surprising that the separation should proceed particularly well if an amount of an amine salt corresponding to the particular proportion of cis-isomer is employed.

The process according to the invention has a number of advantages. Thus the cis-isomers, which are sometimes present in a cis/trans mixture in only minor amount, can be separated off from the bulk of the other isomers, which can be used both for purification and for concentration purposes. Furthermore, the process according to the invention is also suitable for obtaining relatively large amounts of the particular isomers and can be operated continuously.

If, for example, 2 moles of 2,2-dichlorovinyl-3,3-dimethylcyclopropanecarboxylic acid in the form of 1:1 cis/trans mixture is used, and aqueous sodium carbonate solution is used as the alkaline medium, 1 mole of racemic α-methylbenzylamine hydrochloride is used as the amine salt and hydrochloric acid is used as the liberating acid, the course of the reaction can be represented by the reaction scheme which follows:

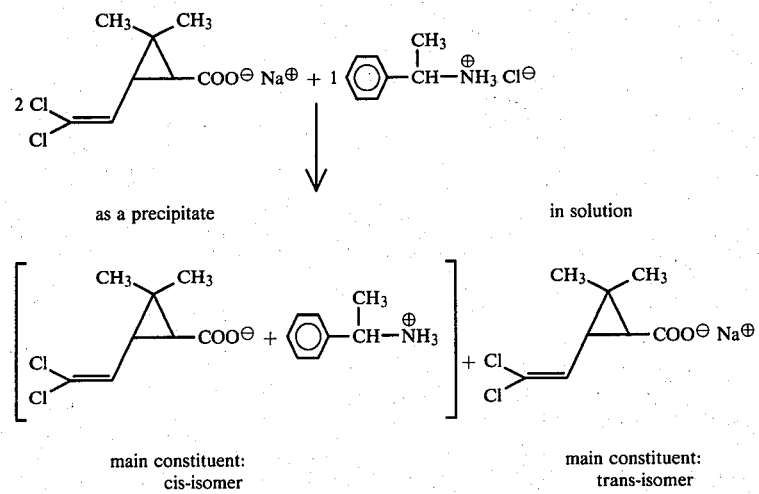

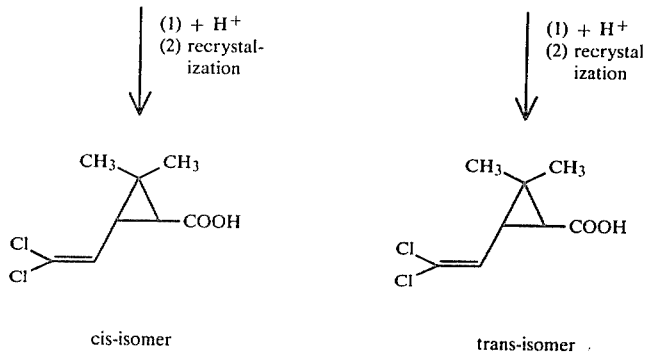

cis-isomer  trans-isomer

In detail, examples which may be mentioned of the compounds which can be separated into stereoisomers by the process according to the invention are: 2-(2,2-dichlorovinyl)-3,3-dimethyl-cyclopropanecarboxylic acid, 2-(2,2-dibromovinyl)-3,3-dimethyl-cyclopropanecarboxylic acid and 2-(2-methylbuten-1-yl)-3,3-dimethyl-cyclopropanecarboxylic acid.

The isomer mixtures, used as the starting material, of substituted vinylcyclopropanecarboxylic acid of the general formula (I) are known (Coll. Czech. Chem. Commun. 24, 2230 (1959); DOS (German Published Specification) 2,615,159; J. Agr. Food Chem. 21, 767 (1973); British Pat. No. 1,446,304; Pestic. Sci. 1971, 245; British Pat. No. 1,413,491; J. Chem. Soc. 1945, 285; DOS (German Published Specification) 2,432,951; J. Org. Chem. 17, 381 (1952) and DOS (German Published Specification) 2,439,177).

Amine salts which can be used in the process according to the invention are preferably salts of arylalkylamines. Examples of these which may be mentioned are the hydrochlorides of benzylamine, α-methylbenzylamine, phenethylamine and amino-phenylacetic acid ethyl ester.

The process according to the invention is carried out in the presence of buffer substances which maintain a constant, weakly alkaline medium. Aqueous solutions of inorganic salts of polybasic acids, such as, for example, of phosphoric acid or carbonic acid, are preferably used for this. Preferred salts include sodium carbonate, potassium carbonate, sodium bicarbonate or sodium hydrogen phosphate.

In the process according to the invention, the cis- and trans-cyclopropanecarboxylic acids are liberated from the corresponding salts by adding strong acids. Preferred acids which can be used here are inorganic acids, such as hydrochloric acid or sulphuric acid, or organic acids, such as formic acid, trichloroacetic acid and trifluoroacetic acid.

In carrying out the process according to the invention, an amount of the amine salt corresponding to the proportion of cis-isomer which was determined by the ratio of the vinylic proton of the cis isomer at 6.2 ppm to that of the proton of the trans isomer at 5.6 ppm in the NMR spectrum and one mole of the buffer substance per mole of isomer mixture of vinylcyclopropanecarboxylic acid are preferably used. The reactants can be brought together at room temperature or under the influence of heat, and the product is then allowed to crystallize out slowly. Whereas the amine salt of the cyclopropanecarboxylic acid, which consists predominantly of the cis-isomer, is the portion which precipitates, as the more sparingly soluble component, the sodium salt of the cyclopropanecarboxylic acid, which consists predominantly of the trans-isomer, remains in solution, as the more readily soluble component. The particular free cyclopropanecarboxylic acids, greatly enriched in cis-isomer or trans-isomer, are obtained from the two salts by adding the equivalent amount of a strong acid. The amine salt thereby liberated can be recycled for use in further precipitations. The pure cis-form and the pure trans-form are obtained by recrystallization. In each case a certain proportion remains in a solution as a 1:1 mixture of cis-isomers and trans-isomers, but this can be re-introduced into the initial precipitation.

Suitable solvents for the recrystallization are non-polar solvents, such as alkanes with up to 8 carbon atoms, petroleum ether or cyclohexane; halogenoalkanes, such as carbon tetrachloride and chlorofluoromethane; and strongly polar solvents, such as aqueous alcohol, ketones or ethers.

The stereoisomeric substituted vinylcyclopropanecarboxylic acids of the formula (I) obtained by the process according to the invention may be used for the preparation of highly active insecticides.

The example which follows illustrates the process according to the invention without indicating a limitation with respect to the extent of its applicability.

EXAMPLE 1 mole of the isomer mixture of 2-(2,2-dichlorovinyl)-3,3-dimethylcyclopropanecarboxylic acid (cis/trans ratio=50/50) was dissolved with 1 mole of sodium carbonate in 1.5 liters of water. 0.5 mole of racemic α-methylbenzylamine hydrochloride in 0.5 liter of water added dropwise to the weakly alkaline solution at 20° C., whereupon a precipitate formed.

The resulting precipitate, that is to say the almost quantitatively formed α-methylbenzylamine salt of the cyclopropanecarboxylic acid, was separated off and shaken with ether and the equivalent amount of hydrochloric acid until all the salt had dissolved. The aqueous phase was separated off and the organic phase was washed again with dilute hydrochloric acid, dried over sodium sulphate and concentrated. Free 2-(2,2-dichlorovinyl)-3,3-dimethylcyclopropanecarboxylic acid was obtained (cis/trans ratio=80/20, determined by NMR).

The pure cis-form crystallized out from petroleum ether, while a 1/1 mixture of the cis-form and trans-form still remained in solution and could be re-introduced into the separation. The aqueous phase contained the amine salt, which had been liberated again, and was recycled for further precipitations.

The free 2-(2,2-dichlorovinyl)-3,3-dimethylcyclopropanecarboxylic acid (cis/trans ratio=20/80 was obtained in a corresponding manner from the aqueous alkaline mother liquor, which contained the dissolved sodium salt of the cyclopropanecarboxylic acid. The pure trans-form crystallized out from petroleum ether at 0° C., while in this case also a 1/1 mixture of the cis-form and trans-form still remained in solution and could also be re-introduced into further separations.

1 mole of the isomer mixture of 2-(2,2-dichlorovinyl)-3,3-dimethylcyclopropanecarboxylic acid (cis/trans ratio=50/50 employed gave 0.3 mole of pure cis-acid, 0.3 mole of pure trans-acid and 0.4 mole of a 1/1 mixture of cis-acid and trans-acid, which can be re-introduced into further separations.

It will be appreciated that the instant specification and example are set forth by way of illustration and not limitation, and that various modifications and changes may be made without departing from the spirit and scope of the present invention.

What is claimed is:

1. A process for the separation of cis- and trans-stereoisomers of a substituted vinylcyclopropanecarboxylic acid of the formula

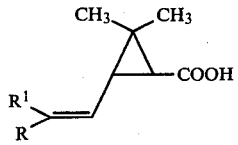

in which
R is alkyl with 1 to 4 carbon atoms, halogen, phenyl or phenyl substituted by at least one of alkyl and halogen, and
$R^1$ is hydrogen, alkyl with 1 to 4 carbon atoms or halogen, or
R and $R^1$, together with the adjacent C atom, form a carbocyclic ring,
comprising reacting the free vinylcyclopropanecarboxylic acid in a weakly alkaline aqueous solution with an amount of an amine salt corresponding to the proportion of cis-isomer present thereby to form a salt precipitate enriched in one of the stereosiomers, separating the precipitate from the supernatant, separately reacting the precipitate and supernatant with a strong acid to liberate the isomeric vinylcyclopropanecarboxylic acid, and recrystallizing at least one of the stereoisomers.

2. A process according to claim 1, wherein R and $R^1$ each is cholorine, bromine or methyl.

3. A process according to claim 1, wherein the amine salt is a salt of an arylalkylamine.

4. A process according to claim 3, wherein the amine salt is the hydrochloride of benzylamine, α-methylbenzylamine, phentylamine or amino-phenylacetic acid ethyl ester.

5. A process according to claim 1, wherein the weakly alkaline medium is maintained by an inorganic salt of a polybasic acid as a buffering agent.

6. A process according to claim 5, wherein the buffering agent is a salt of phosphoric acid or of carbonic acid.

7. A process according to claim 6, wherein the buffering agent is sodium carbonate, potassium carbonate, sodium bicarbonate or sodium hydrogen phosphate.

8. A process according to claim 1, wherein the strong acid is hydrochloric acid, sulphuric acid, formic acid, trichloracetic acid or trifluoracetic acid.

9. A process according to claim 1, wherein recrystallization is effected from an alkane with up to 8 carbon atoms, petroleum ether, cyclohexane, carbon tetrachloride, chlorofluoromethane, aqueous alcohol, a ketone or an ether.

10. A process according to claim 9, wherein R and $R^1$ each is chlorine or bromine, the amine salt is the hydrochloride of benzylamine, α-methylbenzylamine, phenethylamine or amino-phenylacetic acid ethyl ester, the weakly alkaline medium is maintained by sodium carbonate, potassium carbonate, sodium bicarbonate or sodium hydrogen phosphate as a buffering agent, and the strong acid is hydrochloric acid, sulphuric acid, formic acid, trichloracetic acid or trifluoracetic acid, the precipitate being enriched in the cis-stereoisomer.

* * * * *